(12) United States Patent
DeLine et al.

(10) Patent No.: US 7,524,522 B2
(45) Date of Patent: Apr. 28, 2009

(54) KERNEL FRACTIONATION SYSTEM

(75) Inventors: Kenneth E. DeLine, Avon, CO (US); Daniel L. Claycamp, West Frankfort, IL (US); Daniel Fetherston, Cape Girardeau, MO (US)

(73) Assignee: MOR Technology, LLC, Metropolis, IL (US)

( * ) Notice: Subject to any disclaimer, the term of this patent is extended or adjusted under 35 U.S.C. 154(b) by 0 days.

(21) Appl. No.: 11/726,255

(22) Filed: Mar. 21, 2007

(65) Prior Publication Data

US 2008/0044547 A1   Feb. 21, 2008

Related U.S. Application Data

(60) Provisional application No. 60/838,642, filed on Aug. 18, 2006.

(51) Int. Cl.
*A23L 1/10* (2006.01)
(52) U.S. Cl. .................. 426/478; 426/479; 426/481; 426/482; 426/483; 426/518; 426/622
(58) Field of Classification Search ................ 426/478, 426/479, 481, 482, 483, 518, 622
See application file for complete search history.

(56) References Cited

U.S. PATENT DOCUMENTS

| 4,018,755 | A |   | 4/1977  | Wang |
| 4,059,604 | A |   | 11/1977 | Kresse |
| 4,083,836 | A |   | 4/1978  | Anjou et al. |
| 4,181,748 | A | * | 1/1980  | Chwalek et al. ............. 426/623 |
| 4,325,882 | A |   | 4/1982  | Reiners |
| 4,341,713 | A |   | 7/1982  | Stolp et al. |
| 4,495,207 | A |   | 1/1985  | Christianson et al. |
| 4,515,726 | A |   | 5/1985  | Sullivan |
| 4,576,820 | A |   | 3/1986  | Hussmann |
| 4,859,371 | A |   | 8/1989  | Diosady et al. |
| 4,898,673 | A |   | 2/1990  | Rice et al. |
| 4,975,100 | A |   | 12/1990 | Ginelli |
| 4,994,272 | A |   | 2/1991  | Hussmann |
| 5,138,075 | A |   | 8/1992  | Ohgaki et al. |
| 5,250,313 | A |   | 10/1993 | Giguere |
| 5,252,729 | A |   | 10/1993 | De Crosta et al. |
| 5,295,629 | A |   | 3/1994  | Satake et al. |
| 5,498,384 | A |   | 3/1996  | Volk et al. |
| 5,680,812 | A |   | 10/1997 | Linsgeseder |

(Continued)

FOREIGN PATENT DOCUMENTS

CN            1242416          1/2000

(Continued)

OTHER PUBLICATIONS

U.S. Appl. No. 60/838,642, filed Aug. 18, 2006 entitled "Kernel Fractionation Process".

(Continued)

*Primary Examiner*—Helen F Pratt
(74) *Attorney, Agent, or Firm*—CR Miles, P.C.; Craig Miles; Cheryl Anderson

(57) ABSTRACT

Specifically, a dry corn fractionation system which operates to produce an endosperm fraction which can be concurrently of greater purity at greater yield than obtainable from corn milling or dry corn milling processes.

14 Claims, 5 Drawing Sheets

U.S. PATENT DOCUMENTS

| | | | |
|---|---|---|---|
| 5,685,218 | A | 11/1997 | Kemper |
| 5,759,549 | A | 6/1998 | Hiltunen et al. |
| 5,826,500 | A | 10/1998 | Kemper |
| 5,997,877 | A | 12/1999 | Chang |
| 6,201,142 | B1 | 3/2001 | Maza |
| 6,254,914 | B1 | 7/2001 | Singh et al. |
| 6,293,478 | B1 | 9/2001 | Livrieri |
| 6,326,035 | B1 | 12/2001 | Nakatani et al. |
| 6,368,649 | B1 | 4/2002 | van Bommel |
| 6,398,036 | B1 | 6/2002 | Griebat et al. |
| 6,495,175 | B2 | 12/2002 | Rao et al. |
| 6,504,085 | B1 | 1/2003 | Howard |
| 6,570,030 | B2 | 5/2003 | Goto et al. |
| 6,664,405 | B2 | 12/2003 | Lee |
| 6,814,998 | B1 | 11/2004 | Ozawa et al. |
| 6,899,910 | B2 | 5/2005 | Johnston et al. |
| 6,936,110 | B2 | 8/2005 | Van Thorre |
| 6,936,294 | B2 | 8/2005 | Matthews et al. |
| 6,953,165 | B1 | 10/2005 | Griebat et al. |
| 7,037,548 | B2 | 5/2006 | Ozawa et al. |
| 7,074,449 | B1 | 7/2006 | Holley et al. |
| 7,087,720 | B2 | 8/2006 | Murray et al. |
| 7,104,479 | B1 * | 9/2006 | Griebat et al. .................. 241/7 |
| 7,138,257 | B2 | 11/2006 | Galli et al. |
| 7,152,818 | B2 * | 12/2006 | Strissel et al. .................. 241/9 |
| 2003/0019736 | A1 | 1/2003 | Garman |
| 2004/0040895 | A1 | 3/2004 | Fiorini |
| 2004/0234649 | A1 | 11/2004 | Lewis et al. |
| 2005/0233030 | A1 | 10/2005 | Lewis et al. |
| 2005/0239181 | A1 | 10/2005 | Lewis et al. |
| 2006/0035354 | A1 | 2/2006 | Galli et al. |
| 2006/0057251 | A1 * | 3/2006 | Dawley et al. ................ 426/53 |
| 2007/0037267 | A1 | 2/2007 | Lewis et al. |
| 2007/0110862 | A9 * | 5/2007 | Thorre ....................... 426/481 |

FOREIGN PATENT DOCUMENTS

| | | |
|---|---|---|
| CN | 1522596 | 8/2004 |
| GB | 366516 | 1/1932 |
| GB | 707385 | 4/1954 |
| GB | 1058076 | 2/1967 |
| GB | 1398459 | 6/1975 |
| JP | 6136384 | 5/1994 |
| JP | 6299187 | 10/1994 |
| MX | PA99000033 | 9/2004 |

OTHER PUBLICATIONS

Kleber, Mark, Mississippi Renewable Energy Conference—Mar. 25-26, 2003, mg engineering Lurgi PSI, Biodesel Capabilities, 2003, pp. 1-28.

Holcomb, Manual, Harold C. Thompson Jr., Willie M. Cooper and Marvin L. Hopper. SFE Extraction of alfatoxins (B1, B2, G1, and G2) from corn and analysis by HPLC. The Journal of Supercritical Fluids, vol. 9 Issue 2, Jun. 1996, pp. 118-121.

Ronyai, E., B. Simandi, S. Tomoskozi, A. Deak, L. Vigh, and Zs. Weinbrenner. Supercritical fluid extraction of corn germ with carbon dioxide-ethyl alcohol mixture. The Journal of Supercritical Fluids, vol. 14 Issue 1, Oct. 1998, pp. 75-81.

Otles, Semih. Supercritical Fluids and Its Applications in Food Industry. http://eng.ege.edu.tr/~otles/SupercriticalFluids-ScienceAndTechnology/bolumb/Wc197588f62dd7.htm.

Taylor, Scott L. Jerry W. King, and Gary R. List. Determination of Oil Content in Oilseeds by Analytical Supercritical Fluid Extraction. JAOCS, vol. 70 Issue 4, Apr. 1993, pp. 437-439.

Kice Industries, Inc. web site, Multi-Aspirators, http://www.kice.com/products/multiaspirators/index.html, Mar. 19, 2007, seven total pages.

Kice Industries, Inc. web site, Bran Finisher, http://www.kice.com/products/branfinisher/index.html, Mar. 19, 2007, three total pages.

GBS Group, BI-MIX Intensive Dampener product brochure, Sangati Berga, Golfetto, Jun. 2002, three total pages.

GBS Group, Synthesis Rollermill product brochure, Sangati Berga, Golfetto, Jun. 2002, fourteen total pages.

Satake Corporation web site, Maize Degermer VBF product page and brochure, http:/www.satake.co.uk, Mar. 21, 2007, two total pages.

Forsbergs, Inc. web site, cutomer satisfaction page, P-Series Destoners product page, and Vacuum Gravityy Separator, http:/www.forsbergs,com, Mar. 21, 2007, seven total pages.

Great Western Manufacturing web site, "HS" Free Swinging Sifter product brochure, http:/www.gwmfg.com, Mar. 19, 2007, five total pages.

E. Reverchon, G. Della Porta, D. Gorgoglione. Supercritical $CO_2$ fractionation of jasmine concrete. J. Supercrit. Fluids 8 (1995) 60-65.

E. Reverchon, G. Della Porta. Rose concrete fractionation by supercritical $CO_2$. J. Supercrit. Fluids 9 (1996) 199-204.

R. L. Smith Jr., R.M. Malaluan, W.B. Setianto, H. Inomata, K. Arai. Separation of cashew (Anacardium occidentale L.) nut shell liquid with supercritical carbon dioxide. Biores. Technol. 88 (2003) 1-7.

M. A. Rostagno, J.M.A. Araujo, D. Sandi. Supercritical fluid extraction of isoflavones from soybean flour, Food Chem. 78 (2002) 111-117.

L. Sesti Osseo, G. Caputo, I. Gracia, E. Reverchon. Continuous fraction of used frying oil by supercritical CO2. J. Am. Oil Chem. Soc. (JAOCS) 81 (9) (2004) 879-885.

Alberto Bertucco, Francesco Sanmartin and Giuseppe Storti. Simulated moving bed technology for continuous, countercurrent solid-fluid supercritical extraction. The Journal of Supercritical Fluids, vol. 8, Issue 2, Jun. 1995, 138-148.

H. Lee, B.H. Chung and Y. Park. Concentration of tocopherols from soybean sludge by supercritical carbon dioxide.*JAOCS* 68 (1991), p. 571.

G. Brunner, Th. Malchow, K. Stürken and Th. Gottschau. Separation of tocopherols from deodorizer condensates by countercurrent extraction with carbon dioxide. *J. Supercrit. Fluids* 4 (1991), p. 72.

G. Brunner. Gas Extraction—An Introduction to Fundamentals of Supercritical Fluid and the Application to Separation Processes. Springer, Berlin (1994).

J.A. Briones, J.C. Mullins and M.C. Thies. Solvent extraction of fatty acids from natural oils with liquid water at elevated temperatures and pressures.*JAOCS* 67 (1990), p. 852.

P. Bondioli, C. Mariani, A. Lanzani, E. Fefeli and A. Muller. Squalene recovery from olive oil deodorizer distillates.*JAOCS* 70 (1993), p. 763.

O.J. Catchpole and J.C. von Kamp. Extraction of squalene from shark liver oil in a packed column using supercritical $CO_2$.*Ind. Eng. Chem. Res.* 36 (1997), p. 4318.

M.F. Mendes, F.L.P. Pessoa, G.V. Coelho, and A.M.C. Uller. Recovery of the high aggregated compounds present in the deodorizer distillate of vegetable oils using supercritical fluids. JAOCS 34:2, Jun. 2005, pp. 157-162.

D. D. Christianson, J. P. Friedrich, G. R. List, K. Warner, E. B. Bagley, A. C. Stringfellow, G. E. Inglett. Supercritical Fluid Extraction of Dry-Milled Corn Germ with Carbon Dioxide. Journal of Food Science 49 (1), 229-232.

B.M.C. Soares, F.M.C. Gamarra, L.C. Paviani, L.A.G. Goncalves, F.A. Cabral. Solubility of triacyclglycerols in supercritical carbon dioxide. J. Supercrit. Fluids. 2007, 6 total pages.

Ozlem Guclu-Ustundag, Feral Temelli. Correlating the solubility behavior of minor lipid components in supercritical carbon dioxide. J. of Supercritical Fluids 31 (2004) 235-253.

Helena Sovova, Marie Zarevucka, Miroslav Vacek, and Karel Stransky. Solubility of two vegetable oils in supercritical carbon dioxide. J. of Supercritical Fluids 20 (2001) pp. 15-28.

Masturah Markom, Harcharan Singh, and Masitah Hasan. Supercritical $CO_2$ fractionation of crude palm oil. J. of Supercritical Fluids 20 (2001) pp. 45-53.

* cited by examiner

KERNEL FRACTIONATION SYSTEM

This United States patent application claims the benefit of U.S. Provisional Patent Application No. 60/838,642, filed Aug. 18, 2006, hereby incorporated by reference herein.

I. BACKGROUND

Specifically, a dry corn fractionation system which operates to produce an endosperm fraction which can be concurrently of greater purity at greater yield than obtainable from corn milling or dry corn milling processes.

As shown in FIG. 1, certain conventional corn mill processes for ethanol production (1) may mill an amount of whole corn (2) into a mixture of corn particles (3)(referred to hereinafter as "milled corn") which may include particles of corn bran, corn endosperm and corn germ. The milled corn (3) can be transferred to an ethanol production process (4) which includes the conventional steps of fermentation, distillation, and dehydration to generate an amount of ethanol (5). In the fermentation step, the milled corn (3) may be combined with an amount of water and an amount of alpha-amylase (or other enzyme capable of liquefying corn starch) to generate a mash in which the starch of the corn endosperm is liquefied. The mash may be held for a period of time at a temperature of between about 120 degrees Celsius (° C.) and about 150° C. to kill bacteria in the mash. The mash may then be held at a temperature of between about 90° C. and about 100° C. for a duration of time sufficient to achieve a desired level of liquefaction of the starch. An amount of gluco-amylase (or other enzyme capable of generating fermentable sugars from the liquefied starch) added to the mash converts the liquefied starch to fermentable sugars, such as dextrose, in a process referred to as saccharification. Yeast can then be added to the mash to convert the sugars to an amount of ethanol (5) and an amount of carbon dioxide (6) (or CO2) along with other volatile organics. The amount of carbon dioxide (6) can be stored or sold in the marketplace. For sale in to certain markets or for certain applications, the amount of carbon dioxide (6) can be stripped of the other volatile organics and captured as an amount of purified carbon dioxide (9). The fermented mash often referred to as "beer" comprises an amount of ethanol (5) in a concentration of about eight percent to about twenty percent by weight, other liquids and non-fermentable solids. The amount of ethanol (5) in the beer can be separated and concentrated to about 190 proof by conventional distillation techniques and dehydrated by application to molecular sieve to produce a dehydrated ethanol of about 200 proof. The about 200 proof ethanol may be combined with up to about five percent denaturant to generate an amount of fuel ethanol (10).

The stillage which remains after distillation of the beer can comprise an amount of liquid typically referred to as "thin stillage" and an amount of remaining solids typically referred to as the "distillers grains". The thin stillage can be separated from the distillers grains (for example by centrifugation). The distillers grains can be dried by evaporation of the remaining thin stillage to produce "dried distillers grains" ("DDG")(7). The thin stillage can be concentrated by evaporation of water to generate a syrup containing about thirty percent solids (also referred to as "condensed distiller soluble"). The syrup can be recombined with the dried distillers grains to generate an amount of distillers dried grain with solubles (8)("DDGS"). The DDGS can be sold as animal feed.

Even though there is an increasing demand for fuel ethanol (10) worldwide and an increasing amount of research in ethanol production, there remain substantial unresolved problems with respect to conventional ethanol production.

A first substantial problem with conventional corn mill processes for ethanol production (1) can be that milled corn (3) introduced into the ethanol production process (4) which includes particles of corn bran, corn endosperm and corn germ requires an amount of thermal energy (11)(or energy Btus or Btus) to complete the steps of fermentation, distillation and dehydration, and by-product handling. To generate about a gallon of fuel ethanol (5), and a corresponding amount of DDGS (7) and carbon dioxide (6) the ethanol production process (4) utilizing milled corn (3) consumes an amount of thermal energy (11) of between about 30,000 and about 40,000 British thermal units (hereinafter "Btu")(the term "about" as used herein means greater or lesser than the value or range of values stated by 10 percent, but not does not limit any value or range of values to this broader definition and each value or range of values preceded by the term "about" also includes in the alternative the stated absolute value or range of values). This amount of thermal energy (11) is typically generated by burning a corresponding amount of fossil fuel (12) such as oil, coal oil, coal or natural gas. Specifically, inclusion of an amount of non-fermentable biomass or biomass largely non-fermentable, such as corn bran or corn germ, into the ethanol production process requires allocation of an amount of thermal energy (11) to process the amount of non-fermentable biomass; however, this amount of non-fermentable biomass or biomass largely non-fermentable does not produce any or produces very little ethanol which increases the amount of thermal energy (11) per unit of ethanol (5) produced as compared to an ethanol production process in which only the fermentable corn endosperm is processed. Because the corn bran and corn germ represent about 15 percent by weight of the milled corn, if the corn bran and the corn germ can be removed from the ethanol production process, than the amount of thermal energy (11) consumed by the ethanol production process (4) could be substantially reduced.

A second substantial problem with the conventional corn mill process (1) for ethanol production can be that milled corn (3) introduced into the ethanol production process (4) which includes non-fermentable biomass or biomass largely non-fermentable requires allocation an amount of fermenter capacity to biomass which does not produce any or produces very little ethanol. If the corn bran and the corn germ can be removed from the ethanol production process, then the corresponding amount of fermenter capacity freed up could be utilized to process additional fermentable biomass.

A third substantial problem with the conventional corn mill process (1) for ethanol production can be that milled corn (3) introduced into the ethanol production process (4) which includes non-fermentable biomass or biomass largely non-fermentable increases the amount of "distillers grains" produced per unit of ethanol (5) produced. The distillers grains must be dried as above-described to produce dried distiller grains ("DDG") (7) or dried distillers grains with solubles ("DDGS")(8). The drying of "distillers grains" can be the single largest point of energy consumption in the ethanol production process (4). If the corn bran and the corn germ can be removed from the ethanol production process (5), then a corresponding reduction in the amount "distillers grains" can be achieved with a corresponding reduction in the amount of thermal energy (11) utilized to produce DDG per unit of ethanol (5) produced.

A fourth substantial problem with conventional corn mill processes for ethanol production can be that the market for conventional DDG (7) by products may become saturated as the number of ethanol production facilities increases. Conventional DDG (7) includes corn bran as the amount of corn bran is increased in the DDG (7) the percent protein by weight decreases. As the percent protein by weight of the DDG (7) decreases the value of the DDG (7) or DDGS (8) as a feed. Additionally, inclusion of corn bran in the DDG increase the fat content of the DDG which can make the DDG unacceptable as a feed for poultry and fish.

Now referring primarily to FIG. 2, an alternative to conventional corn mill processes (1) can be a dry corn mill process (13) which facilitates isolation of a corn bran fraction (15), a corn germ fraction (16), and a corn endosperm fraction (14). The corn endosperm fraction (14) generated from the conventional dry corn mill process (13) can be introduced into an ethanol production process (4) above-described to in part address certain of the above-identified problems. However, because the primary function of the conventional dry corn mill process (13) is to facilitate the production of a lowered-fat grit or meal for the production of food products such as cereal, table grits or the like, the conventional dry corn mill process (13) including hardware and methods of utilizing the hardware have not been optimized to provide a corn endosperm fraction (14) for introduction into an ethanol production process (4). As such, overall process yield of the corn endosperm fraction (14) useful in the ethanol production process (4) has never been the primary goal of the dry corn mill process (13) and as such corn endosperm recovery is typical sacrificed to increase corn endosperm purity. However, loss of corn endosperm in the context of an ethanol production process (4) solely to increase corn endosperm purity can result in significant economic losses.

To address the unresolved problems of conventional corn mill processes and conventional dry corn milling above-described the instant inventive dry corn fractionation system generates isolated corn fractions including a bran fraction, a germ fraction, and an endosperm fraction with high purity and at high yield which can be utilized independent of the other in proportioned recombination in the ethanol production process.

II. SUMMARY OF THE INVENTION

Accordingly, a broad object of the invention can be to provide a dry corn fractionation system which operates to isolate a corn bran fraction, a corn germ fraction, and a corn endosperm fraction which have a greater purity coupled with a greater yield than conventional dry corn milling.

Another broad object of the invention can be to provide a corn endosperm fraction of not less than about seventy percent purity by weight coupled with an overall corn endosperm loss of not greater than about six percent by weight or even not greater than four percent by weight.

Another broad object of the invention can be to provide a dry corn fractionation system which includes as an initial step kernel breakage which generates a population of corn particles which have a greater size whether individually or as a population than compared to the first kernel breakage step of a conventional corn mill process.

Another broad object of the invention can be to provide a kernel breaker which operates to provide the kernel breakage which generates the population of corn particles which have a greater size whether individually or as a population than compared to the first kernel breakage step of a conventional corn mill process.

Another broad object of the invention can be to provide a first aspiration step and a second aspiration step coupled directly after the kernel breakage step and directly before a sifting step to remove bran and fines containing moisture to increase the efficiency of the sifting step.

Another broad object of the invention can be to provide a bran finishing step coupled directly after the second the second aspiration step which operates to remove corn endosperm associated with the bran fraction aspirated from second aspirator and return the removed corn endosperm to the sifting step.

Another broad object of the invention can be to provide a first density separation and a second density separation coupled directly after the sifting step the second density separation being the final step in the dry corn mill system which yields a corn endosperm fraction of greater than seventy percent purity by weight with a overall loss of corn endosperm fraction of not greater than about four percent by weight.

Another broad object of the invention can be to couple the corn fractionation system to an ethanol production process to decrease thermal energy consumption, increase ethanol production capacity, and produce a high protein dried fractionated corn gluten meal whether independently or in various combinations and permutations.

Naturally, further objects of the invention are disclosed throughout other areas of the specification, drawings, and claims.

III. A BRIEF DESCRIPTION OF THE DRAWINGS

IV. DETAILED DESCRIPTION OF THE PREFERRED EMBODIMENTS

A dry corn fractionation system which operates to produce an endosperm fraction which can be concurrently of greater purity at greater yield than the corn milling or dry corn milling processes.

Figure 1:
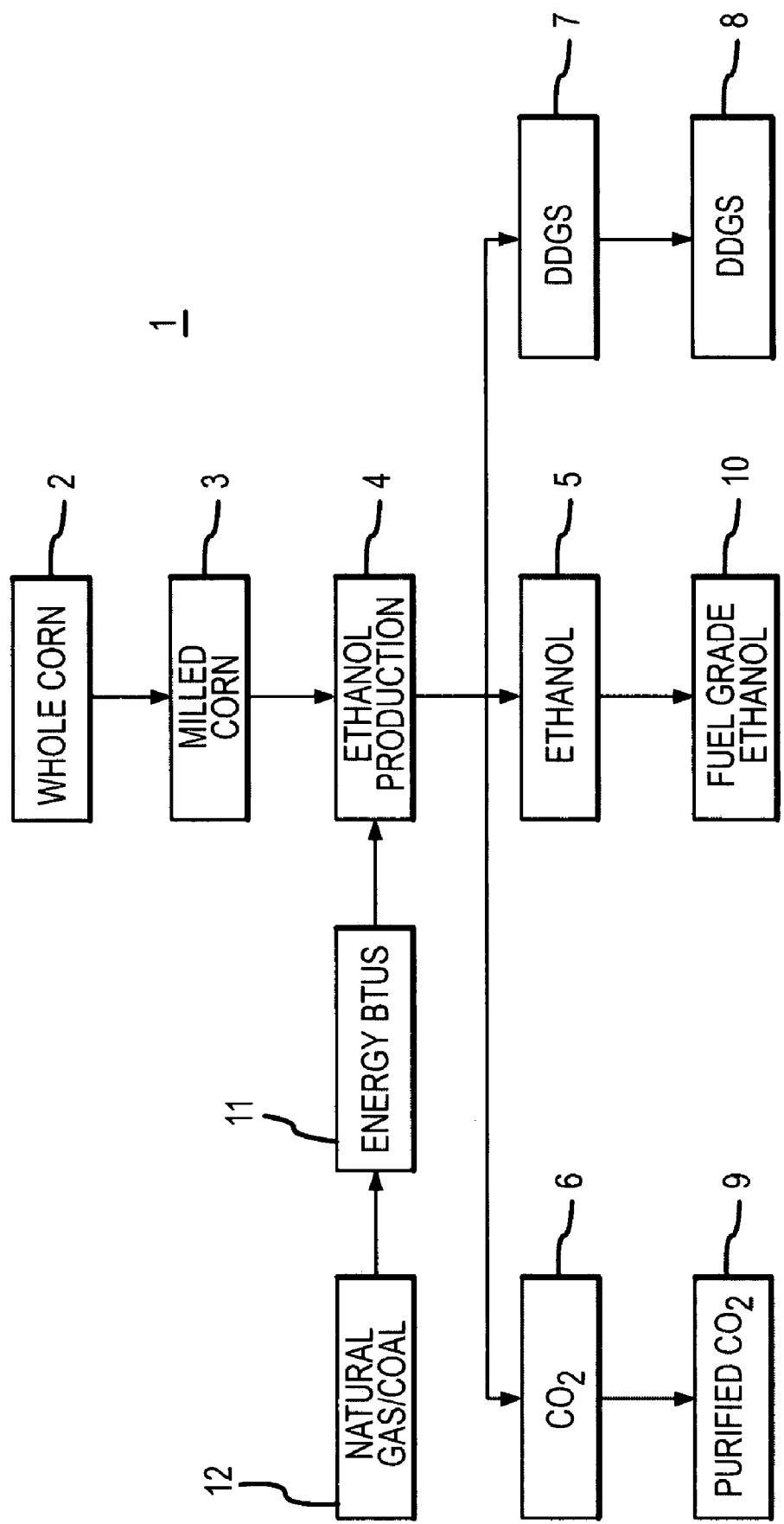
FIG. 1 is a block flow diagram of a conventional corn mill process which generates milled corn coupled to a ethanol production process.
Figure 2:
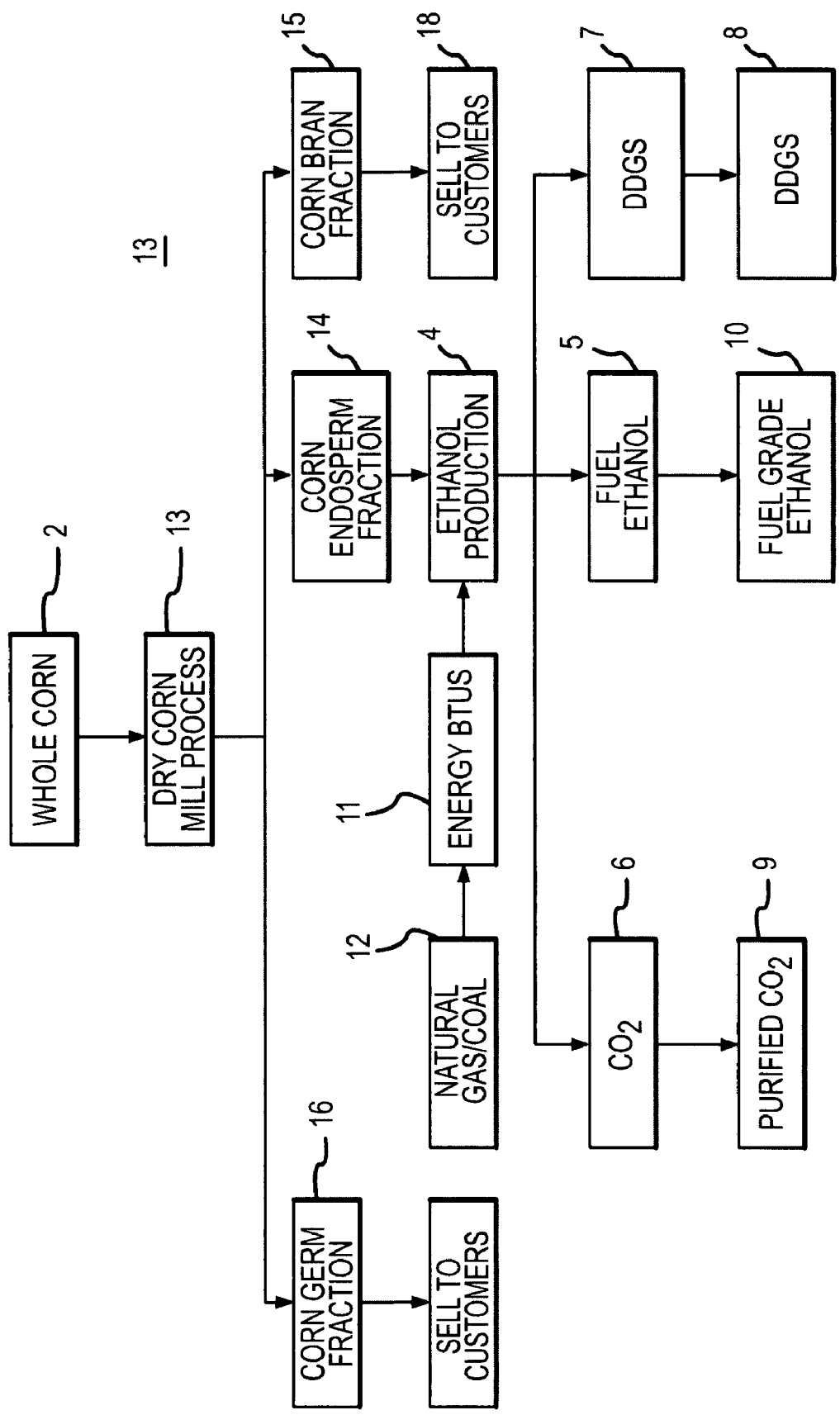
FIG. 2 is a block flow diagram of a dry corn mill process which generates corn fractions coupled to a ethanol production process.
Figure 3:
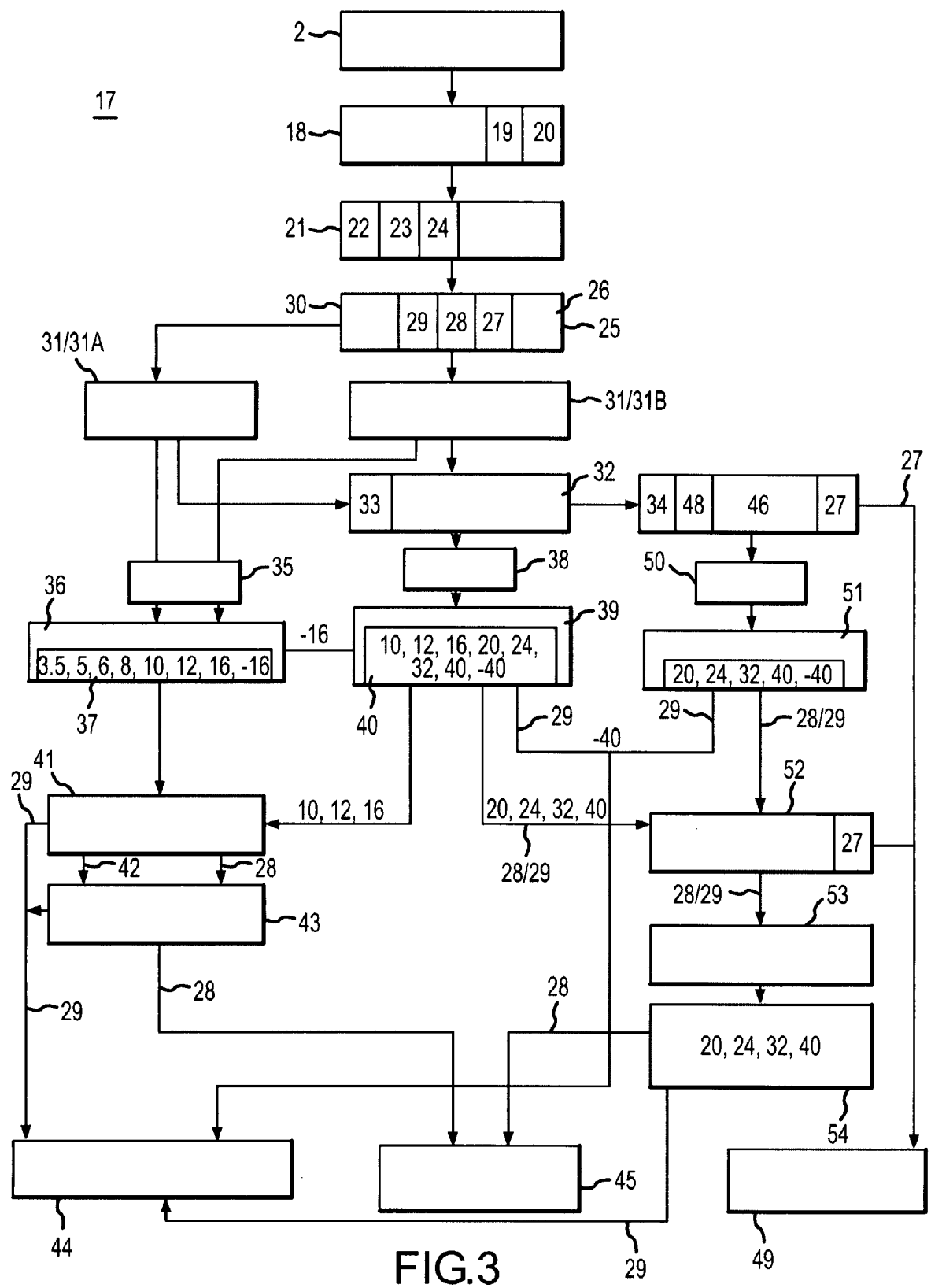
FIG. 3 is a block flow diagram of the inventive corn fractionation system which generates corn fractions coupled to a ethanol production process.

First referring primarily to FIG. 3, the dry corn fractionation system (17) whole corn (2) can be received and accepted by a corn cleaner (18). Whole corn (2) can move along a first sloping deck of the corn cleaner (18) having a plurality of holes. Whole corn (2) can pass through the holes onto an second sloping deck thereby removing material larger than a kernel of whole corn (2). The whole corn (2) then moves along the second sloping deck having holes of lesser size then a kernel of whole corn (2) thereby removing material smaller than a kernel of whole corn (2). The corn cleaner (18) can further include a cleaner aspirator (19). Whole corn (2) then passes through the cleaner aspirator (19) (as a non-limiting example a Series E six path unit available from Kice Industries, Inc., 5500 North Mill Heights Drive, Wichita, Kans.) to remove material having lesser density than a kernel of whole corn (2). The corn cleaner (18) can further include a de-stoner (20) which removes materials of greater density than a kernel of whole corn (2). The term "whole corn" as used herein broadly encompasses kernels of corn removed from the cob regardless of the variety or grade. Additionally, it is not intended that the example of a corn cleaner (18) be limited to above-described configuration and any manner of corn cleaning which results in whole corn (2) which is substantially free of materials that are not whole corn (2) can be utilized with the various embodiments of the dry corn fractionation system (17).

The whole corn (2) substantially free of other materials can be accepted by a corn temper process (21). The whole corn (2) cleaned of other materials can be transferred by a conveyor (22) (as a non-limiting example a Bi-Mix 30-55/180-22 available from GBS Group S.p.a, Corso Uniti, 7, Padova, Italy). As the whole corn (2) moves up the inclined conveyor (22), water and steam can be introduced to the whole corn (2) and mixed by the the conveyor (22)(by paddles, screws, or the like). The whole corn (2) leaves the conveyor and drops into a temper tank (23). The whole corn (2) resides in the temper tank (23) for a duration of time of between about five minutes and fifteen minutes to allow the water to be distributed over the entire kernel of whole corn (2) and absorbed by the bran coat until the bran coat reaches a pre-selected target moisture.

Figure 4:
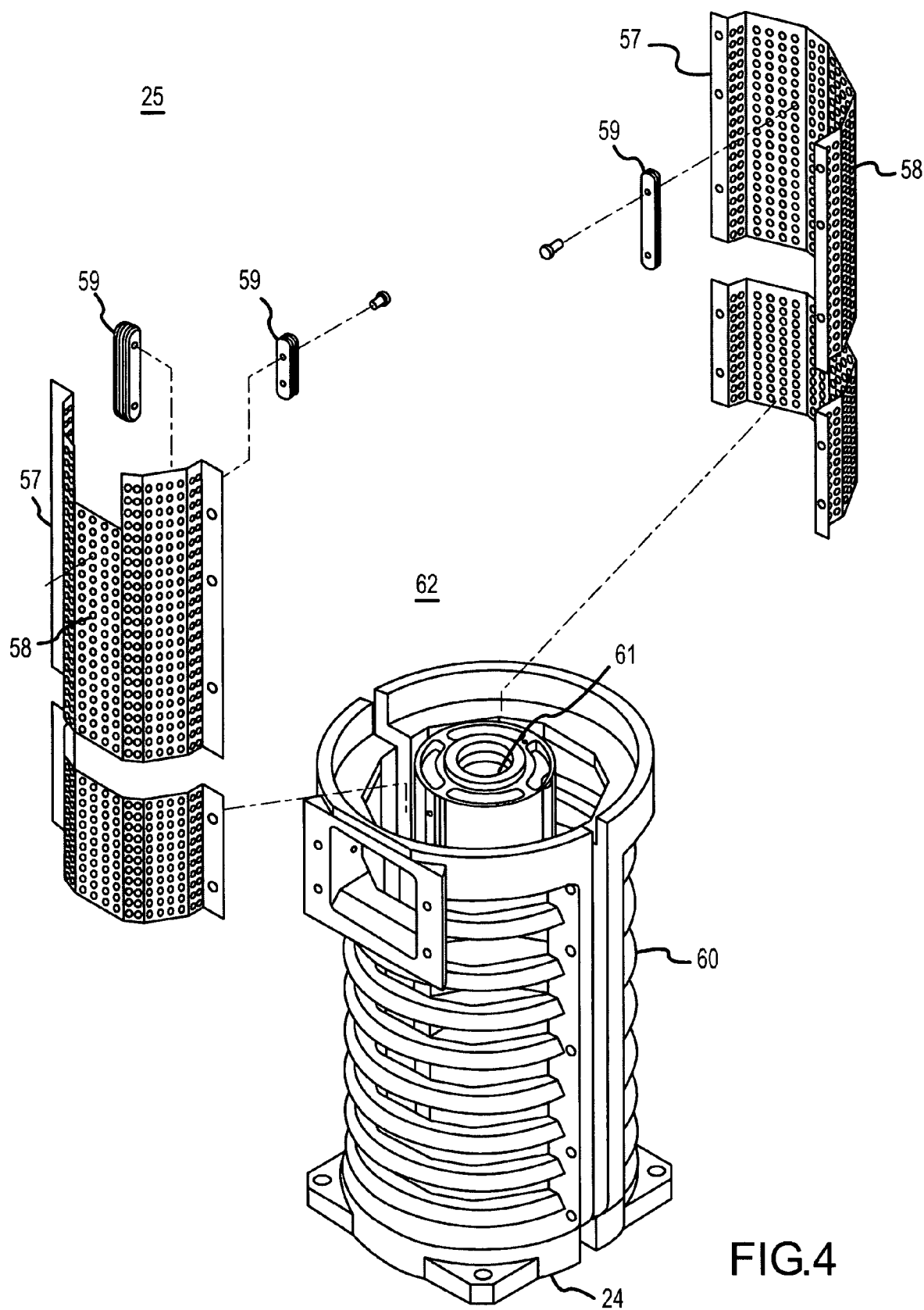
FIG. 4 is an exploded view of a part of a Satake Maize Degermer modified to produce an embodiment of the dry corn mill granulation.

Again referring primarily to FIGS. 3 and 4, after tempering a plurality of kernels of whole corn (24) can be accepted by a kernel fracture assembly (25) which breaks the whole corn (2) into a plurality of corn particles (26). The initial breakage of the plurality of kernels of whole corn (24) which generates a mixture of a plurality of corn bran particles (27), a plurality of corn germ particles (28) and a plurality of corn endosperm particles (29) affects the success of all subsequent fractionation steps in the inventive dry corn fractionation system (17). Numerous and varied kernel fracture assemblies (25) can be utilized to generate the plurality of corn particles (26) having a size or a range of sizes suitable for use in the dry corn fractionation system (17). One non-limiting kernel fracture assembly (25) suitable for use in the inventive dry corn fractionation system (17) can be a modified Satake Maize Degermer, model VBF 10AM-L available from Satake Corporation, 2-30, Saijo, Nishiho-machi, Higashihiroshia-shi, Hiroshima, Japan.

Now referring primarily to FIG. 4, the Satake Maize Degermer (shown in part) can be altered or modified to produce the plurality of particles (26) suitable for use with the inventive dry corn fractionation system (17) by replacing the conventional slotted screens having a plurality of 0.8 mm slots with perforated screens (57) each having a plurality of perforations (58) of about the same number as the conventional slots and each being substantially circular having diameter in the range of between about 5 millimeters ("mm") to about 10 mm with certain embodiments having diameter of between about 6 mm to about 9 mm and with certain embodiments having a diameter of between about 6 mm to about 8 mm. The non-limiting embodiment of the perforated screens as shown in the figure can have a plurality of perforations (58) of be about 7 mm. However, the desired size distribution of the plurality of corn particles (26) may be obtained utilizing other perforation configurations and the invention is not limited solely to substantially circular perforations but to any configuration of perforation which can yield the inventive particle size distribution described herein. The plurality of perforations (58) can have be located at the same or similar locations of the prior conventional slots, however, the invention is not so limited and the location or placement pattern of the plurality of perforations (58) can be any location or placement which yields the inventive particle size distribution described herein.

Additionally, the conventional 4 mm breaker bars (often referred to as "clickers") can be replaced with modified breaker bars (59) of between about 6 mm to about 10 mm at substantially the same locations as the conventional clickers, or replacing both (see FIG. 4 which shows the modified screens (58) with modified breaker bars (59) which can be fit to a conventional Satake Maize Degermer). Again, based on the configuration and placement of the plurality of perforations (58), embodiments of the invention can utilize unmodified clickers, or modified breaker bars (59) which generate the particle size distribution of the plurality of particles (26) described herein. Alternately, as to certain embodiments the clickers can be modified and the plurality of perforations configured to the extent necessary to generate the particle size distribution described herein. As a particular embodiment of the invention as shown in the figures, both the plurality of perforations (58) and the modified breaker bars (59) can be utilized to produce the particle size distribution described herein.

With respect to the operation of the modified Satake Maize Degermer, the plurality of kernels of whole corn (24) enter the bottom of a substantially vertical cylinder (60) and become located between the surface of a rotating drum (61) and the inside walls (62) of the steel cylinder (60) to become fractured by kernel on steel impact and by kernel on kernel impact into the plurality of corn particles (26). A part of the plurality of corn particles (26) pass through the perforations in the walls of the steel cylinder (referred to as the "throughs"). The remaining plurality of corn particles (26) pass over the top of the steel cylinder (referred to as the "tails"). FIG. 4 does not show the additional parts of the Satake Maize Degermer which can be utilized without modification as shown in the company catalog.

By modifying the Satake VBF Maize Degermer as above-described, the size distribution of the plurality of corn particles (26) generated substantially changes with respect to the "tailstock" and the "through stock". Referring first to Table 1 below fracturing of a plurality of whole corn kernels (24) with a conventional Satake VBF can result in amount of "tailstock" of about 73 percent by weight of the plurality of corn kernels (25) introduced into the Satake VBF Degermer. The size distribution of the "tailstock" held by a 3.5 wire, a 4 wire, a 5 wire, a 6 wire, an 8 wire, or a 10 wire sifter and the amount passing through the 10 wire sifter to the pan are shown as percents by weight of the total weight of the plurality of whole corn kernels (24) introduced into the Satake VBF Maize Degermer and as a percent of the total weight of the tailstock generated. Similarly, as shown by Table 2 fracturing of a plurality of whole corn kernels (24) results in a conventional amount of "throughstock" of about 22 percent by weight of the plurality of corn kernels (24) introduced into the Satake VBF Degermer. The size distribution of the "throughstock" held by a 6 wire, a 4 wire, a 10 wire, a 14 wire, an 18 wire, a 24 wire, and a 40 wire sifter, and passing through the 40 wire sifter to the pan are shown respectively as a percent by weight of the total weight of the plurality of whole corn kernels (24) introduced into the Satake Degermer and as a percent total weight of the throughstock generated.

Now comparing the size distribution of the plurality of particles (26) conventionally generated to the size distribution of the plurality of particles (26) generated by the non-limiting example of the modified Satake VBF Maize Degermer as above described and utilized in the inventive dry corn fractionation system (17), it can be understood that the size distribution for the "tailstock" and the "throughstock" generated by the modified Satake VBF Maize Degermer falls in a narrower range of particle size with lesser of the plurality of corn particles (26) held by the 3.5 wire screen (typically re-fractured) and with a reduction in the plurality of particles (26) having a size lesser than can be held by a 10 wire screen. As such, the vast majority of the plurality of particles (26) produced by the inventive corn fracture assembly (25) fall in the range of −3.5 wire (falling through a 3.5 wire screen) and +10 wire (retained by a 10 wire screen). As compared to the conventional range of −3.5 wire and +40. Note, that the amount of −10 particles (falling through a 10 wire screen) for the tailstock and the through stock combined is reduced by about 15 percent to about 25 percent over the conventional corn fracture process. Also the amount of fines −40 wire (falling through a 40 wire screen) produced by the inventive corn fracture assembly is substantially reduced. Reduction in the amount fines significantly lower water content of the plurality of particles and allows subsequent steps in the inventive dry corn fractionation system (17) to operate without or a reduced aggregation of particles.

TABLE 1

Conventional Corn Particle Size Distribution Of Tailstock Generated By A Conventional Satake Maize Degermer.

| Wires/In. | % Retained Of Total Whole Corn | % Total Retained Of Tailstock |
|---|---|---|
| Sifted Tails |  | 72.98% |
| 3.5 | 31.77% | 23.19% |
| 4 | 7.75% | 5.66% |
| 5 | 22.38% | 16.33% |
| 6 | 15.28% | 11.15% |
| 8 | 10.92% | 7.97% |
| 10 | 5.35% | 3.90% |
| pan (−10) | 6.55% | 4.78% |
| Total | 100.00% | 72.98% |

TABLE 2

Conventional Corn Particle Size. Distribution Of Throughstock Generated By A Conventional Satake Maize Degermer.

| Wires/In. | % Retained Of Total Whole Corn | % Total Retained Of Tailstock |
|---|---|---|
| Sifted Throughs |  | 21.51% |
| 6 | 0.00% | 0.00% |
| 10 | 0.57% | 0.12% |
| 14 | 1.00% | 0.22% |
| 18 | 8.14% | 1.75% |
| 24 | 15.14% | 3.26% |
| 40 | 28.43% | 6.11% |
| pan (−40) | 46.71% | 10.05% |
| Total | 100.00% | 21.51% |

TABLE 3

Corn Particle Size Distribution Of Tailstock Generated By A Modified Satake Maize Degermer.

| Wires/In. | % Retained Of Total Whole Corn | % Total Retained Of Tailstock |
|---|---|---|
| Sifted Tails |  | 24.87% |
| 3.5 | 28.80% | 7.16% |
| 4 | 15.72% | 3.91% |
| 5 | 38.54% | 9.58% |
| 6 | 12.17% | 3.03% |

TABLE 3-continued

Corn Particle Size Distribution Of Tailstock Generated By A Modified Satake Maize Degermer.

| Wires/In. | % Retained Of Total Whole Corn | % Total Retained Of Tailstock |
|---|---|---|
| 8 | 3.04% | 0.76% |
| 10 | 1.01% | 0.25% |
| pan (−10) | 0.71% | 0.18% |
| Total | 100.00% | 24.87% |

TABLE 4

Corn Particle Size Distribution Of Throughstock Generated By Modified Satake Maize Degermer.

| Wires/In. | % Retained Of Total Whole Corn | % Total Retained Of Tailstock |
|---|---|---|
| Sifted Throughs | % | 53.90% |
| 3.5 | 1.28% | 0.69% |
| 4 | 4.84% | 2.61% |
| 5 | 28.31% | 15.26% |
| 6 | 29.02% | 15.64% |
| 8 | 17.78% | 9.58% |
| 10 | 9.25% | 4.98% |
| pan (−10) | 9.53% | 5.14% |
| Total | 100.00% | 53.90% |

Understandably, numerous and wide variety of kernel fracture assemblies (25) can be adjusted or modified to generate the in the dry corn mill fractionation system (17) to generate a plurality of corn particles (26) having a comparable particle size distribution to Tables 3 and 4 (the term "comparable" meaning the combined weight percent of the corn particles retained by screens between about 4 wire screen and about a ten wire screen to the total weight of the unfractured whole corn (2) is not reduced by an amount greater than about 10 percent) whether in a plurality of particle streams, two streams such as "tailstock" and "throughstock", or as a single stream so long as the particle size distribution over the streams generated by kernel fracture assembly remains comparable or yields an even greater weight percent of the plurality of particles (26) of +4 to about +10 than described herein. Understandably the goal is to generate a plurality of particles (26) which are the fewest in number and greatest in size which can still be utilized to separate the plurality of kernels of whole corn (24) into the constituent parts including corn bran, corn germ and corn endosperm. (the inventive "dry corn mill granulation")(30). Production of the dry corn mill granulation (30) is considered to be encompassed by or a part of the inventive dry corn fractionation system (17), or as an isolated step an invention in itself without more. The dry corn mill granulation having not been described before the instant patent application and providing a solution to a substantial problem in corn fractionation and the problem of developing a corn fractionation system compatible with ethanol production.

Again referring primarily to FIG. 3, the plurality of particles (26) generated by the corn fracture assembly (25) (which as to certain embodiments of the invention can have the size distribution of the dry mill granulation (30) above-described) can be passed through a first aspirator (31)(or a plurality of first aspirators in parallel) and a second aspirator

(32) (or a plurality of second aspirators in parallel) to separate an aspirated stream of the plurality of corn bran particles (27) from a non-aspirated stream comprising a mixture of the plurality of corn endosperm particles (29) and the plurality of corn germ particles (28). The aspirated stream of the plurality of corn bran particles (27) can contain certain particles of corn endosperm attached to a part of the plurality bran particles (27) and certain particles of corn endosperm and certain particles of corn germ of sufficiently low mass to be aspirated by the first aspirator (31). As such, the non-limiting embodiment of the aspiration step shown in FIG. 3, the "tails" and the "throughs" from kernel fracture assembly (25) of the modified Satake Degermer each separately pass separately through a first aspirator (31A)(31B) to generate a mixture of the plurality of corn endosperm particles (29) and the plurality of corn germ particles (28) and a first aspirated plurality of corn particles (33). The first aspirated plurality of corn particles (33) passes through the second aspirator (32) to generate a mixture of the plurality of corn endosperm particles (29) and the plurality of corn germ particles (28) and a second aspirated plurality of corn particles (34) which largely contains the plurality of corn bran particles (27) but also contains some amount of the plurality of corn germ particles (28) and some amount of the plurality of corn endosperm particles (29). A non-limiting example of the first aspirator(s) (31) and the second aspirator(s) (32) can be a Kice, Series E six path unit available from Kice Industries, Inc., 5500 North Mill Heights Drive, Wichita, Kans. The determination of the correct air setting for the first aspirator (31A) through which the "tails" pass and the first aspirator (31B) through which the "throughs" pass can be made by achieving a particle profile which includes mixture of the plurality of corn endosperm particles (29) and plurality of corn germ particles (28) comprising about 95% of the non-aspirated stream by weight of each of the first aspirators (31). An advantage of utilizing a first aspiration step and a second aspiration step over conventional process methods can be removal of the plurality of corn bran particles (27) and part of the plurality of corn endosperm particles (29) and part of the plurality of corn germ particles (27) of sufficiently low mass to be aspirated in the first and second aspirated plurality of corn particles (33)(34) which contain the vast majority of the water content in the plurality of particles (26) delivered from the corn fracture assembly (25) which allows for more ready sifting of the non-aspirated mixture (35) of the plurality of corn endosperm particles (29) and the plurality of corn germ particles (28).

Again referring primarily to FIG. 3, the non-aspirated mixture (35) of the plurality of corn endosperm particles (29) and the plurality of corn germ particles (28) from the first aspirator(s)(31)(31A)(31B) can be accepted by a first sifter (36) which generates a plurality of streams of sifted particles (37) by retaining a part of the plurality of corn endosperm particles (29) and a part of the plurality of corn germ particles (28) on a plurality of screens between the range of about 3.5 wires per inch to about 16 wires per inch. A certain non-limiting embodiment of the first sifter (36) can have a 3.5 wire screen, a 5 wire screen, a 6 wire screen, a 10 wire screen, a 12 wire screen, and a 16 wire screen although other combinations of screens in the range could also be utilized. Similarly, the non-aspirated mixture (38) of the plurality of corn endosperm particles (29) and corn germ particles (28) from the second aspirator (32) can be accepted by a second sifter (39) to generate a plurality of streams (40) of endosperm particles (29) and corn germ particles (28) by retaining a part of the plurality of corn endosperm particles (29) and a part of the plurality of corn germ particles (28) on a plurality of screens between the range of about 10 wires per inch to about 40 wires per inch. A certain non-limiting embodiment of the second sifter (39) can have a 10 wire screen, a 12 wire screen, a 16 wire screen, a 20 wire screen, a 24 wire screen, a 32 wire, and a 40 wire screen although other combinations of screens in the range can be utilized. The second sifter (39) in the embodiment shown can also accepts the −16 particles (particles falling through a 16 wire screen) from the first sifter (36)(although these corn particles not retained by the first sifter (36) will be the pass through of the smallest selected screen). As a non-limiting example, a Great Western "HS" Sifter available from Great Western Manufacturing, 2017 South 4$^{th}$ Street, Leavenworth, Kans. 66048-0149 can be suitable for use as above-described.

Of the plurality of streams of sifted particles (37)(40) generated by the first sifter (36) and the second sifter (39) of greater than about 16 wire can be accepted by a corresponding plurality of first gravity separators (41). In the non-limiting example provided above each of the plurality of streams of sifted particles (37)(40) retained by the 5 wire screen, the 6 wire screen, the 8 wire screen, the 10 wire screen and the 16 wire screen can be accepted by a corresponding one of the plurality of first gravity separators (41). Each of the plurality of first gravity separators (41) can generate three separator streams including a plurality of corn endosperm particles (29); a mixture of corn endosperm particles and corn germ particles (42), and a plurality of corn germ particles (28). The separator streams which include the plurality of corn endosperm particles (29) from each first separator (41) can be accepted in a corn endosperm fraction storage unit (44). The separator streams including the mixture of corn endosperm particles and the plurality of corn germ particles (42), and the plurality of corn germ particles (28) can each be accepted by a corresponding one of a plurality of second gravity separators (43) each of which generates two second separator streams including the plurality of corn endosperm particles (29) and the plurality of corn germ particles (28). The plurality of corn endosperm particles (29) can be accepted by the corn endosperm fraction storage unit (44) and the plurality of corn germ particles (28) accepted by a corn germ fraction storage unit (45). A non-limiting example of a gravity separator can be a Forsberg Vacuum Gravity Separator, Model 50-VMS available from Forsberg, Inc., P.O. Box 510, 1210 Pennington Avenue, Thief Rivers Falls, Minn. 56701. A plurality of corn germ particles (28) can the range of about 20 wire to about 40 wire which can be accepted by third aspirator (46).

The second aspirated plurality of corn particles (34) from the second aspirator (32) can be accepted by a corn bran finisher (46). The corn bran finisher (46) operates to remove an amount of bound corn endosperm (48) from the plurality of corn bran particles (27) to generate an unbound mixture of the plurality of corn endosperm particles and the plurality of corn germ particles (50) and a stream of corn bran particles (27). As a non-limiting example, a Kice Bran Finisher, Model BF42 can be utilized to accept the second aspirated plurality of corn particles (34).

The stream of the plurality of corn bran particles (27) can be accepted by a corn bran fraction storage unit (49). The unbound mixture of the plurality of corn endosperm particles and the plurality of corn germ particles (50) can be accepted by a third sifter (51) having a range of screens between about 20 wires per inch and 40 wires per inch. A non-limiting example of a third sifter (51) can provide a 20 wire screen, a 24 wire screen, a 32, wire screen, and a 40 wire screen. A suitable third sifter (51) can be a Great Western "HS" Sifter. The plurality of corn germ particles (28) retained by the third sifter (51) in the range of between about the 20 wire screen and the 40 wire screen can be accepted by a third aspirator (52) along with the plurality of corn germ particles (28) retained by the second sifter (39) in the range of between about the 20 wire screen and the 40 wire screen. The plurality of corn endosperm particles (29) passing through the 40 wire screen of the second sifter (39) and the third sifter (51) can be accepted by the corn endosperm fraction storage unit (44).

The non-aspirated stream from the third aspirator (52) comprised largely of a plurality of corn germ particles (28) can be accepted by a plurality of roller mills (53) which operate to increase the size of the plurality of corn germ particles (28) and reduce the size of the plurality of corn endosperm particles (29). A suitable non-limiting example of a roller mill can be a Model 100/30-4A Pick-Up available from GBS Group S.p.a, Corso Stati, 7- Padova- Italy. The plurality of corn germ particles (28) and the plurality of corn endosperm particles (29) from each roller mill (53) can be accepted by a fourth sifter (54) having a plurality of screens in the range of between about 20 wires per inch and about 40 wires per inch. The plurality of corn germ particles (28) retained by the plurality of screens between about 20 wires per inch and about 40 wires per inch can be accepted by the corn germ fraction storage unit (45). The plurality of corn endosperm particles (29) which pass through the screen having about 40 wires per inch can be accepted by the corn endosperm storage unit (44).

The inventive dry corn fractionation system (17) can produce end material balances by weight percent for each corn fraction (44)(45)(49), as follows:

Germ %: about 8.0 to about 9.0
Bran %: about 6.0 to about 6.4
Endosperm %: about 85.0 to about 86.0

In addition to the end material balances by weight percent for each fraction (44)(45)(49), the inventive dry corn fractionation system (17), can as to certain embodiments produce each corn fraction with advantageous ratios of fat, fiber, and starch by weight percent, as follow:

|  | Fat % | Fiber % | Starch % |
|---|---|---|---|
| Germ Fraction (45) | 20% min. | 25% max. | 18.0% max. |
| Bran Fraction (49) | 6% max. | 75% min. | 15.0% max. |
| Endosperm Fraction (44) | 1.5% max. | 2.0% max. | 82.5% min. |

Additionally, certain embodiments of the inventive dry corn fractionation system (17) can achieve these advantageous ratios and material balances concurrently which allows a high purity endosperm fraction (44) of at least about 82% with starch loss (compared to clean whole corn (2)) of not greater than about 4%.

Figure 5:
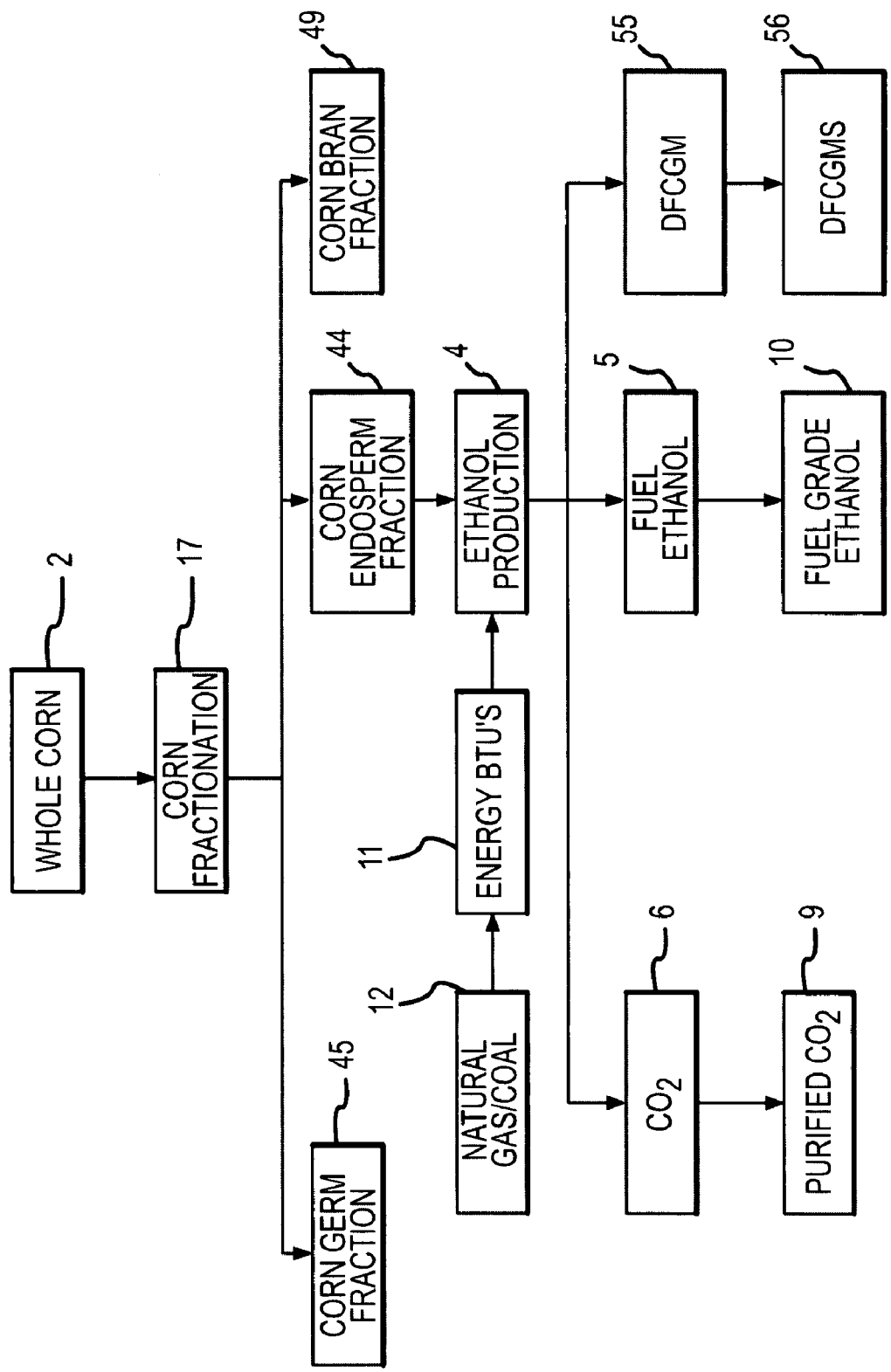
FIG. 5 is a block flow diagram of an embodiment of the inventive dry corn mill fractionation system.

Now referring primarily to FIG. 5, the corn endosperm fraction (44) generated by the inventive dry corn fractionation system (17) can be coupled to a various configurations of an ethanol production process (4) to increase the amount of ethanol (5) produced, reduce the amount of thermal energy used per unit of ethanol (5) produced, reduce the cost per unit of ethanol (5) produced, and to produce in substitution of the DDG an amount of a high protein dried fractionated corn gluten meal (55)("DFCGM") which can be mixed with solubles to produce a high protein high protein dried fractionated corn gluten meal with solubles (56)("DFCGMS"). Embodiments of suitable configurations of the ethanol production process (4) which can be coupled to the endosperm fraction (44) generated by the inventive corn fractionation system (17) are described for example by Patent Cooperation Treaty Application No. PCT/US2006/045193, hereby incorporated by reference.

As can be easily understood from the foregoing, the basic concepts of the present invention may be embodied in a variety of ways which includes the best mode of the invention. The invention involves numerous and varied corn germ oil extraction devices and methods of extracting corn oil from corn germ whether derived from conventional corn milling processes, from the kernel fractionation processes incorporated by reference, or otherwise. While certain examples are provided in the context of dry corn fractionation processes, it is not intended that these examples limit the use of the invention to corn germ derived solely from these inventive dry corn fractionation process (17), but rather are intended to be illustrative such that a person of ordinary skill in the art can make and use the invention in the context of the numerous and varied processes that produce an amount of corn germ from which corn germ oil (23) can be extracted.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "mill" should be understood to encompass disclosure of the act of "milling"—whether explicitly discussed or not—and, conversely, were there effectively disclosure of the act of "milling", such a disclosure should be understood to encompass disclosure of a "mill" and even a "means for milling." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

Thus, the applicant(s) should be understood to claim at least: i) each of the dry corn fractionation devices or systems herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth below are intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A method of kernel fractionation, comprising the steps of:
    a. tempering a plurality of kernels of whole corn;
    b. providing a corn kernel fracture assembly;
    c. fracturing a plurality of corn kernels to generate a plurality of corn particles, wherein said plurality of corn particles comprise a mixture of a plurality of corn bran particles, a plurality of corn germ particles, and a plurality of corn endosperm particles; and
    d. aspirating said plurality of corn particles to separate said plurality of corn bran particles from said plurality of corn endosperm particles and said plurality of corn germ particles, wherein aspirating said plurality of corn particles to separate said plurality of corn bran particles consisting essentially of:
        i. aspirating said plurality of corn particles with a first aspirator; and
        ii. aspirating said plurality of corn particles with a second aspirator.

2. A method of kernel fractionation as described in claim 1, wherein said step of fracturing said plurality of corn kernels to generate said plurality of corn particles comprises the step of generating the fewest number of corn particles which can be separated into said plurality of corn bran particles, said plurality of corn germ particles, and said plurality of corn endosperm particles.

3. A method of kernel fractionation as described in claim 2, wherein said step of generating the fewest number of corn particles which can be separated into said plurality of corn bran particles, said plurality of corn germ particles, and said plurality of corn endosperm particles step comprises the step of generating a dry corn mill granulation.

4. A method of kernel fractionation as described in claim 3, further comprising the steps of:
    a. finishing said aspirated plurality of corn bran particles to remove an amount of bound corn endosperm and an amount of bound corn germ;
    b. generating a plurality of finished corn bran particles; and
    c. generating an unbound mixture of said plurality of corn endosperm particles and said plurality of corn germ particles.

5. A method of kernel fractionation as described in claim 4, further comprising the steps of:
    a. sifting each said mixture of said plurality of corn endosperm particles and said plurality of corn germ particles;
    b. generating a first sifted stream of said plurality of corn endosperm particles and said plurality of said corn germ particles which are retained by a 16 wire screen;
    c. generating a second sifted stream of said plurality of corn endosperm particles and said plurality of corn germ particles which are retained by a 40 wire screen; and
    d. generating a third sifted stream of said plurality of corn endosperm particles which pass through said 40 wire screen.

6. A method of kernel fractionation as described in claim 5, further comprising the step of performing a first density separation said first sifted stream to generate:
    a. a first density separated stream of said plurality of corn endosperm particles;
    b. a second density separated stream of said plurality of corn germ particles; and
    c. a third density separated stream of a mixture of said plurality of corn endosperm particles and said plurality of corn germ particles.

7. A method of kernel fractionation as described in claim 6, further comprising the step of performing a second density separation on a mixture of said second density separated stream and said third density separated stream to generate:
    a. a first density separated stream of said plurality of corn endosperm particles; and
    b. a second density separated stream of said plurality of corn germ particles.

8. A method of kernel fractionation as described in claim 5, further comprising the step of aspirating said second sifted stream to remove an amount of said plurality of bran particles.

9. A method of kernel fractionation as described in claim 8, further comprising the step of rolling said second sifted stream to increase size of said plurality of corn germ particles and to reduce size of said plurality of corn endosperm particles.

10. A method of kernel fractionation as described in claim 9, further comprising the step of sifting said second sifted stream to separate said plurality of corn germ particles having increased size from said plurality of corn endosperm particles having reduced size.

11. A method of kernel fractionation as described in claim 10, further comprising the step of combining the plurality of corn endosperm particles to establish a corn endosperm fraction having a purity by weight selected from the group consisting of: not less than about 70 percent by weight, not less than about 75 percent by weight, not less than about 80 percent by weight, not less than about 85 percent by weight, not less than about 86 percent by weight, not less than about 87 percent by weight, and not less than 88 percent by weight.

12. A method of kernel fractionation as described in claim 11, wherein said step of combining the plurality of corn endosperm particles to establish a corn endosperm fraction which has a starch loss by weight of not greater than four percent by weight.

13. A method of kernel fractionation as described in claim 11, wherein said step of combining the plurality of corn endosperm particles to establish a corn endosperm fraction which has a starch loss by weight of not greater than three percent by weight.

14. A method of kernel fractionation as described in claim 11, wherein said step of combining the plurality of corn endosperm particles to establish a corn endosperm fraction which has a starch loss by weight of not greater than about 2.5 percent by weight.

* * * * *